United States Patent
Bogdanovic et al.

(10) Patent No.: US 6,225,508 B1
(45) Date of Patent: May 1, 2001

(54) METHOD FOR PRODUCING ALKANALS USING A RHODIUM-TRI-POLYETHYLENE GLYCOLATE

(75) Inventors: Sandra Bogdanovic, Frankfurt am Main; Herbert Roesky, Gottingen; Uwe Ritter, Gottingen; Thomas Borrmann, Gottingen, all of (DE)

(73) Assignee: Hoechst Research & Technology Deutschland GmbH & Co. KG (DE)

( * ) Notice: Subject to any disclaimer, the term of this patent is extended or adjusted under 35 U.S.C. 154(b) by 0 days.

(21) Appl. No.: 09/462,399

(22) PCT Filed: Jun. 25, 1998

(86) PCT No.: PCT/EP98/03896

§ 371 Date: Feb. 15, 2000

§ 102(e) Date: Feb. 15, 2000

(87) PCT Pub. No.: WO99/02477

PCT Pub. Date: Jan. 21, 1999

(30) Foreign Application Priority Data

Jul. 7, 1997 (DE) ............................................. 197 28 944

(51) Int. Cl.[7] .................................................... C07C 45/50
(52) U.S. Cl. ............................ 568/454; 568/451; 556/137
(58) Field of Search ................................ 568/451, 456; 556/137

(56) References Cited

U.S. PATENT DOCUMENTS 4,158,020 * 6/1979 Stautzenberger et al. ..... 260/604 HF
4,329,511  5/1982 Hackman et al. .................... 568/454

FOREIGN PATENT DOCUMENTS

2326489 * 12/1974 (DE) .
2291960   6/1976 (FR) .
54-042391 * 4/1979 (JP) .

OTHER PUBLICATIONS

Yan et al, "Aqueous–phase. . . Phosphine", Chemical Abstracts, vol. 125, No. 3, Jul. 15, 1996, Abstract No. 033125.

* cited by examiner

Primary Examiner—Sreeni Padmanabhan
(74) Attorney, Agent, or Firm—Bierman, Muserlian and Lucas

(57) ABSTRACT

According to the invention, branched and straight chain alkenes and cycloalkenes with five and more C-atoms are by means of hydroformylation using a novel rhodium-tri-polyethylene glycolate of a polyethylene glycol with an average molecular weight of 320 to 650 as a catalyst with at hydrogen/carbon monoxide pressure of 60 to 200 bar and at a temperature of between 50 and 150° C. converted into branched and straight chain alkanals and cycloalkanals with six and more C-atoms. The reaction is preferably carried out in water or polyethylene glycol or a mixture of the same as a solvent in the heterogeneous phase. The aldehydes obtained are easy to separate from the catalyst in the reaction preparation. Said aldehydes are also obtained with a high level of purity and a high yield.

15 Claims, No Drawings

METHOD FOR PRODUCING ALKANALS USING A RHODIUM-TRI-POLYETHYLENE GLYCOLATE

This application is a 371 of PCT/EP98/03896 filed Jun. 25, 1998.

The present invention relates to the technical field of hydroformylation of olefins.

The present invention achieves the object of preparing, in particular, relatively high molecular weight linear and branched and also cyclic alkanals by hydroformylation of corresponding olefins by means of a rhodium tri (polyethylene glycolate) as high-activity catalyst in high yield and purity and isolating them from the reaction mixture in a simple manner.

The hydroformylation of olefins to aldehydes using a noble metal complex is known. Thus, U.S. Pat. No. 4,329,511 describes the reaction of olefins with hydrogen and carbon monoxide to give aldehydes in inert high-boiling solvents, with the catalyst used being a noble metal of transition group VIII complexed by, for example, a triorganophosphine such as triphenylphosphine. The high-boiling solvent has to have a molecular weight of at least 700 when ethylene is used as starting olefin and of at least 1500 in the case of higher olefins. These high-boiling solvents are said to dissolve the catalyst and enable the catalyst to be reused after the alkanal formed has been isolated from the reaction mixture by distillation or by stripping with an inert gas. However, this procedure has, like all hydroformylation reactions of olefins carried out in a single phase using a metal catalyst, the considerable disadvantage that the alkanal, in particular one containing over 10 carbon atoms, can be separated off by distillation only with considerable difficulty, if at all, because of its high boiling point; apart from losses of the alkanal end product, not inconsiderable amounts of heavy oils are formed as decomposition products. The hydroformylation process described in this U.S. Pat. No. 4,329,511 is therefore only economically feasible for the synthesis of lower alkanals such as those having up to 7 carbon atoms. To drive relatively high molecular weight, high-boiling alkanals out of the reaction mixture, the reaction gases (carbon monoxide, hydrogen and olefin) have to have a temperature of over 250° C.

The hydroformylation of olefins by the processes of the published European Patent Application No. 0 314 435 and U.S. Pat. No. 4,613,701 is carried out similarly; in these processes, as a consequence of the disadvantages discussed here, only low molecular weight olefins are used in the reaction.

Furthermore, DE-A 2 552 351 describes the reaction of olefins with hydrogen and carbon monoxide in the presence of a rhodium salt such as rhodium chloride, rhodium sulfate and rhodium nitrate in water or an alkanol as reaction medium and solvent with addition of a lower polyethylene glycol having up to three ethoxy units. This lower polyethylene glycol is supposed to prevent precipitation of the rhodium salt from the reaction solution. This process, too, is carried out in a single phase and has the abovementioned disadvantages.

In contrast, two-phase catalyst systems using a solvent which does not dissolve the alkanal formed offer technical advantages. The phase containing the catalyst can be separated from the alkanal formed without additional process steps. In addition, it is not absolutely necessary to isolate the catalyst after the reaction if the polar phase containing the catalyst can be used in a continuous hydroformylation process in which alkanal formed can also be separated off during the process. Such a process is known, for example, from DE-A 2 627 354 in which linear olefins are hydroformylated in water as solvent in the presence of a rhodium-triphenylphosphine complex containing sulfo groups. However, this procedure does not allow relatively long chain olefins, e.g. those having more than 5 carbon atoms, to be reacted, since the yield of the alkanals obtainable therefrom is unsatisfactory because of the insufficient activity of the catalyst in the case of relatively high molecular weight olefins. In addition, the phosphine which has the function of forming a complex with the rhodium has to be used in a considerable excess, for example up to a 100-fold excess based on the rhodium.

According to the present invention, a two-phase hydroformylation process for olefins using a novel catalyst has now been found, which process overcomes the abovedescribed disadvantages of the prior art and enables even relatively high molecular weight linear and branched and also cyclic olefins to be hydroformylated in high yield and purity and makes it possible to easily separate the alkanals formed from the reaction mixture, even in a continuous process.

The present invention accordingly provides a process for preparing linear and branched aliphatic monoaldehydes (alkanals) having from 6 to 21 carbon atoms, preferably from 7 to 19 carbon atoms, and cyclic aliphatic monoaldehydes having from 6 to 13 carbon atoms by hydroformylation of linear and branched aliphatic monoolefins (alkenes) having from 5 to 20 carbon atoms, preferably from 6 to 18 carbon atoms, or cyclic olefins having from 5 to 12 carbon atoms, i.e. by reacting such olefins with a carbon monoxide/hydrogen gas mixture, using a rhodium catalyst, wherein the reaction is carried out in a heterogeneous phase by means of a rhodium tri(polyethylene glycolate) of a polyethylene glycol having a mean molecular weight of from 320 to 650, preferably from 350 to 450, particularly preferably 400, at a temperature of from 50 to 150° C., preferably from 80 to 120° C., and at a pressure of from 60 to 200 bar, preferably from 75 to 120 bar. The rhodium tri(polyethylene glycolate) is preferably used in the reaction in the form of a solution in water, in polyethylene glycol having the mean molecular weight indicated or a mixture of this polyethylene glycol with water as solvent.

The rhodium tri(polyethylene glycolate) serving as catalyst is a new compound in which polyethylene glycol is bound as glycolate to the rhodium. The present invention thus also provides rhodium tri(polyethylene glycolate) compounds in which the polyethylene glycol moiety has a mean molecular weight of from 320 to 650, preferably from 350 to 450, particularly preferably a mean molecular weight of 400. The invention further provides solutions of a rhodium (tri)polyethylene glycolate) according to the invention in water, in polyethylene glycol or in a polyethylene glycol/water mixture as solvent, in each case using a polyethylene glycol having a mean molecular weight of from 320 to 650, preferably from 350 to 450, particularly preferably 400.

The novel rhodium tri(polyethylene glycolate) compounds can be assigned the formula (1)

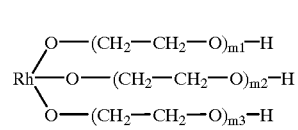

(1)

where $m_1$, $m_2$ and $m_3$, are identical or different and are each a number from 6 to 15, preferably from 7 to 11, and one third of the sum ($m_1+m_2+m_3$) is from about 6.8 to about 14.4, preferably from about 7.55 to about 9.8. The rhodium tri(polyethylene glycolate) compound of the invention can advantageously be prepared by heating rhodium(III) chloride trihydrate with the polyethylene glycol in the stochiometric amount (i.e. in an amount which is 3 times the equivalent amount) at a temperature of from 40 to 80° C., preferably from 50 to 65° C., advantageously under a stream of nitrogen and at atmospheric pressure or slightly subatmospheric pressure, with the hydrogen chloride gas formed being removed. The compound is a stoichiometric compound and is readily miscible with water and a polyethylene glycol having a mean molecular weight of from 320 to 650. It can also be synthesized under the same conditions using an excess of polyethylene glycol so as to form the solution of the rhodium tri(polyethylene glycolate) in polyethylene glycol straight away, and this solution can, if appropriate mixed with water, advantageously be used in the hydroformylation reaction.

Olefins which are used in the hydroformylation process of the invention are, for example, 1-hexene, 1-octene, 1-decene, 1-dodecene, 1-tetradecene, 2-hexene, 2-heptene, 2-octene, 2,4,4-trimethyl-1-pentene, 2,4,4-trimethyl-2-pentene, cyclohexene, cyclooctene and 4-methyl-1-cyclohexene.

The hydroformylation of the invention is generally carried out by placing the rhodium tri(polyethylene glycolate), dissolved in a polyethylene glycol having the specified average molecular weight, in a mixture of such a polyethylene glycol with water or in water alone, in an autoclave, pressurizing the gas space of the autoclave with a carbon monoxide/hydrogen gas mixture to a pressure within the specified range, with the autoclave being heated to the desired reaction temperature before, during or after the injection of the carbon monoxide/hydrogen gas mixture, and subsequently introducing the olefin into the reaction mixture while maintaining the reaction pressure and continuing to stir the solution. The reaction mixture obtained in this way is then reacted for a number of hours at the desired reaction temperature and the reaction pressure while continuing to stir. After cooling and venting the autoclave, the mixture formed is separated into the aldehyde phase and the polyethylene glycol solution phase or aqueous phase. However, in the case of appropriately constructed autoclaves, the hydroformylation can also be carried out continuously, i.e. by continuous addition of the reactants to the rhodium tri(polyethylene glycolate) solution with continuous removal of the aldehyde phase formed. In the batchwise procedure, the catalyst phase separated off can be returned to the autoclave for catalyzing a further batch.

The aldehyde phase which can be separated off after the reaction is complete consists of virtually pure aldehyde (virtually no transfer of rhodium to the aldehyde phase can be detected) which does not have to be further purified, for example by distillation, for further use. In this respect, the process of the invention is particularly advantageous for the synthesis of relatively high-boiling alkanals such as those having more than 10 carbon atoms.

In the hydroformylation, 1-olefins, i.e. olefins having a terminal double bond, give a mixture of isomeric alkanals in which the aldehyde group is in the 1 and 2 positions of the aliphatic radical. In general, addition of particular secondary and tertiary amines or cyclic amines in the hydroformylation reaction enables a selectivity favoring the 1-alkanal to be achieved. Such compounds are, for example, piperidine, pyridine, 3-methylpyridine, dialkylamines having alkyl radicals of from 1 to 4 carbon atoms each, e.g. dimethylamine and in particular diethylamine and dipropylamine, and also trialkylamines having alkyl radicals of from 1 to 4 carbon atoms each, e.g. triethylamine. These amines are generally used in an amount of up to 0.5% by weight, based on the olefin.

The carbon monoxide/hydrogen gas mixture used for the reaction generally comprises equimolar amounts of hydrogen and carbon monoxide, but it is also possible, without disadvantages, for one of these reactants to be present in the gas mixture in an excess of up to 50%, hydrogen even up to an excess of 100%.

In general, the carbon monoxide/hydrogen gas mixture introduced into the autoclave is present in the reaction space in a molar excess of up to 2 based on the olefin used, depending on the corresponding pressure of the gas mixture which is chosen. Although the reactants can initially also be present in the reaction mixture in a molar ratio to the olefin, the presence of the reactants hydrogen and carbon monoxide in excess is advantageous, especially since they can easily be removed from the autoclave after the reaction is complete.

The weight ratio of the water, ethylene glycol or polyethylene glycol/water phase in which the rhodium tri (polyethylene glycolate) is dissolved to the olefin can be from 10:1 to 1:3 at the beginning of the reaction; a weight ratio of from 2:1 to 1:2 has been found to be particularly advantageous. The molar ratio of the rhodium tri (polyethylene glycolate) catalyst in the possibly water-containing polyethylene glycol phase to the olefin can be controlled by the proportion of polyethylene glycol or polyethylene glycol/water mixture as solvent. Based on the rhodium itself, the molar ratio to the olefin can be from 1:900 to 1:20000. Preference is here given to a molar ratio of rhodium to olefin at the beginning of the reaction in the range from 1:1800 to 1:12000, preferably from 1:4000 to 1:10000; in the case of branched olefins, a ratio of from 1:1800 to 1:5000 is generally also advantageous.

The reaction time for the hydroformylation of the olefin in the process of the invention can be a plurality of hours and can, depending on reaction temperature, reaction pressure and the specific olefin, be from 2 to 15 hours.

The use of the rhodium tri(polyethylene glycolate) catalyst of the invention has the advantage that its activity does not decrease even in the case of relatively long-chain olefins such as those having more than 9 carbon atoms. In addition, branched olefins and olefin mixtures which, according to experience, are more difficult to hydroformylate than linear olefins can also be hydroformylated particularly advantageously according to the invention.

The following examples serve to illustrate the invention. The percentages and parts are by weight, unless indicated otherwise. Parts by weight bear the same relationship to parts by volume as that of the kilogram to the liter.

EXAMPLE A

To synthesize the pure rhodium tri(polyethylene glycolate), rhodium(III) chloride trihydrate is reacted in stoichiometric amounts with polyethylene glycol having an average molecular weight of 400:

10 parts of rhodium(III) chloride trihydrate are heated to 60° C. with 16 parts by volume of polyethylene glycol 400 passing a stream of nitrogen over the mixture, and the mixture is held at this temperature for two days under a stream of nitrogen.

The compound obtained is a dark red oil having a viscous to solid consistency. It is completely miscible with water, likewise with polyethylene glycol, and dissolves in acetonitrile. While warming gently at 50° C., the oil is held under a reduced pressure of 0.01 bar for about 8 hours so as to virtually completely remove remaining hydrogen chloride gas which has formed during the reaction. This gives virtually chloride-free rhodium tri(polyethylene glycolate).
Analysis:
Rhodium content: 19.9%; chloride content: 200 ppm;
IR spectrum (film, KBr): 3449, 2098, 1956, 1740, 1649 cm$^{-1}$:
Absorption maximum in the UVNIS region: 445 nm;
$^1$H NMR (in d$_7$-acetonitrile; reference: tetramethylsilane): δ=3.4–3,6 ppm (multiplets).

EXAMPLE B

To synthesize a solution of rhodium tri(polyethylene glycolate) of a polyethylene glycol 400 in polyethylene glycol 400 as solvent, 5 parts of rhodium(III) chloride trihydrate are dissolved in 150 parts by volume of polyethylene glycol having a mean molecular weight of 400, the solution is stirred for 3 hours at 40° C. while passing a gentle stream of nitrogen over it to remove the hydrogen chloride gas formed, and the pressure in the reaction vessel is then reduced to 0.01 bar to remove remaining traces of hydrogen chloride gas.

Subsequent analysis indicates complete conversion in the reaction and that the solution no longer contains any chloride ions. The rhodium content of the solution is 13 parts of rhodium per liter of polyethylene glycol 400.

EXAMPLE 1

5 parts by volume of the rhodium catalyst solution prepared as described in Example B are mixed with 195 parts by volume of polyethylene glycol 400 having a water content of 1% and are introduced into an autoclave whose gas space is then filled with an equimolar mixture of hydrogen and carbon monoxide under a total pressure of 80 bar. The solution is heated to 100° C. while stirring, this temperature is held for another 3 hours while continuing to stir and while maintaining the pressure of 80 bar, and 200 parts by volume of 1-hexene are then added while continuing to maintain the previous reaction conditions, the reaction mixture is stirred for another two hours and, after cooling and venting the autoclave, the reaction mixture obtained is transferred to a phase separator. The upper phase comprising the aldehyde synthesized is separated from the lower phase, viz. the polyethylene glycol solution containing the rhodium catalyst which can be returned to the autoclave for a new batch.

Gas-chromatographic analysis of the product phase separated off indicates a heptanal content of 98%; the remaining 2% consist predominantly of unreacted 1-hexene and isomerized hexene (2-hexene). The ratio of 1-heptanal to 2-heptanal, i.e. linear to branched heptanal, is 0.75. The yield of heptanal is 98% of theory.

EXAMPLE 2

The procedure of Example 1 is repeated, but the 1-hexene is replaced by the same amount of 1-octene and the 5 parts by volume of the solution of the rhodium catalyst are replaced by 10 parts by volume thereof in making up the reaction mixture. After the reaction is complete, the aldehyde phase is separated off. It comprises up to 99% of a mixture of 1-nonanal and 2-nonanal in a yield of 99% of theory and a molar ratio of 1- to 2-nonanal of 0.5.

EXAMPLE 3

The hydroformylation of 1-octene is carried out using the procedure described in Example 2, but 0.002 parts of pyridine is additionally added to the reaction mixture together with the 1-octene.

After separating off the nonanal phase, a 1-nonanal/2-nonanal mixture in a ratio of 1.7 is obtained in a yield of 89% of theory and a purity of 89% (the remaining components are essentially unreacted 1-octene and 2-octene). The addition of pyridine has thus favored the selectivity to the linear nonanal.

EXAMPLE 4

The hydroformylation of 1-octene is carried out using the procedure described in Example 1, but 0.005 parts of pyridine is additionally added to the reaction mixture together with the 1-octene.

After separating off the nonanal phase, a 1-nonanal/2-nonanal mixture in a ratio of 1.9 is obtained in a yield of 96% of theory and a purity of 96% (the remaining 4% consist essentially of unreacted 1-octene and 2-octene). The addition of pyridine has thus favored the selectivity to the linear nonanal.

EXAMPLE 5 a) To synthesize a solution of rhodium tri(polyethylene glycolate) of a polyethylene glycol 600 in polyethylene glycol 600 as solvent, 10 parts of rhodium(III) chloride trihydrate are dissolved in 150 parts by volume of polyethylene glycol having a mean molecular weight of 600, the solution is stirred for three hours at 40° C. while passing a gentle stream of nitrogen over it to remove the hydrogen chloride gas formed and the pressure of the reaction vessel is then reduced to 0.01 bar to remove remaining traces of hydrogen chloride gas.

b) 10 parts by volume of the resulting solution of the rhodium catalyst are mixed with 195 parts by volume of polyethylene glycol 600 20 having a water content of 2% and introduced into an autoclave. The gas space of the latter is filled with an equimolar mixture of hydrogen and carbon monoxide under a total pressure of 80 bar. The mixture is heated while stirring to 100° C., this temperature is held for another three hours while continuing to stir and while maintaining the pressure of 80 bar, 200 parts by volume of 1-octene are then added while maintaining the previous reaction conditions and the reaction mixture is stirred for another two hours. After cooling and venting the autoclave, the aldehyde phase is separated off; this phase contains 79% of nonanal (the remaining 21% consist predominantly of unreacted 1-octene and isomerized octene). The ratio of 1-nonanal to 2-nonanal, i.e. linear to branched nonanal, is 1.2. The yield of nonanal is 79% of theory.

EXAMPLE 6

10 parts by volume of the rhodium catalyst solution prepared as described in Example B are mixed with 195 parts by volume of polyethylene glycol 400 having a water content of 2% and are introduced into an autoclave whose gas space is then filled with an equimolar mixture of hydrogen and carbon monoxide under a total pressure of 80 bar. The solution is heated while stirring to 100° C., this temperature is held for another three hours while continuing to stir and while maintaining the pressure of 80 bar, 200 parts by volume of 1-dodecene are then added while maintaining a temperature of about 100° C. and a pressure of about 80 bar and the reaction mixture is stirred for another two hours. After cooling and venting the autoclave, the aldehyde phase is separated off. Gas-chromatograph analysis of the product phase separated off indicates a tridecanal content of 99%; the remaining components are predominantly unreacted 1-dodecene and 2-dodecene formed by isomerization. The ratio of 1-tridecanal to 2-tridecanal, i.e. linear to branched tridecanal, is 1.1. The yield of tridecanal is 99.0% of theory.

EXAMPLE 7

The hydroformylation of 1-dodecene is carried out using the procedure described in Example 5b), but replacing the 1-octene by the same amount of 1-dodecene. Separating off the tridecanal phase gives a 1-tridecanal/2-tridecanal mixture in a ratio of 0.2 and a yield of 88.0% of theory and a purity of 88%.

EXAMPLE 8

20 parts by volume of the rhodium catalyst solution prepared as described in Example B are mixed with 800 parts by volume of polyethylene glycol 400 having a water content of 2% and are introduced into an autoclave whose gas space is then filled with an equimolar mixture of hydrogen and carbon monoxide under a total pressure of 80 bar. The solution is heated while stirring to 100° C., this temperature is held for another three hours while continuing to stir and while maintaining the pressure of 80 bar and 800 parts by volume of 2-hexene are then added while maintaining these reaction conditions, the reaction mixture is stirred for another two hours at 100° C. and 80 bar and, after cooling and venting the autoclave, the reaction mixture obtained is transferred to a phase separator in which the aldehyde phase having a heptanal content of 96% is separated off. As a result of the partial isomerization of 2-hexene to 1-hexene, this gives a mixture of 1-heptanal and 2-heptanal in a mixing ratio of 0.83. The yield of heptanal mixture is 96% of theory.

EXAMPLE 9

The procedure of Example 8 is repeated, but the 2-hexene is replaced by the same amount of a mixture of 1-hexene and 2-hexene in a mixing ratio of 1:1 and the 5 parts by volume of the rhodium catalyst solution prepared as described in Example B are replaced by 10 parts by volume thereof when making up the reaction mixture. This gives a mixture of 1-heptanal and 2-heptanal in a ratio of 0.9 and a yield of 94% of theory.

EXAMPLE 10

4 parts by volume of the rhodium catalyst solution prepared as described in Example B are mixed with 300 parts by volume of water and introduced into an autoclave whose gas space is then filled with an equimolar mixture of hydrogen and carbon monoxide under a total pressure of 100 bar. The mixture is heated while stirring to 100° C., this temperature is held for another three hours while continuing to stir and while maintaining the pressure of 100 bar and 320 parts by volume of 2,4,4-trimethyl-1-pentene are then added under these conditions. The reaction mixture is held at 100° C. for another five hours while continuing to stir, and, after cooling and venting the autoclave, the reaction mixture obtained is transferred to a phase separator. The aldehyde phase is separated from the aqueous phase containing the rhodium catalyst which can be returned to the autoclave for a new batch.

Gas-chromatographic analysis of the product phase separated off indicates the following composition:

| 3,5,5-trimethyl-1-hexanal | 92%; | 2-t-Butyl-3-methyl-1-butanal | 0.5% |
|---|---|---|---|
| 2,4,4-trimethyl-1-pentene | 3.4%; | 2,4,4-Trimethyl-2-pentene | 1.2% |
| 2,4,4-trimethylpentane | 1.2%; | 3,5,5-Trimethyl-1-hexanol | 0.4%; |
| nonvolatile compounds | 1.2%. | | |

EXAMPLE 11

The procedure of Example 10 is repeated, but the olefin used there is replaced by the same amount of its isomer 2,4,4-trimethyl-2-pentene.

Gas-chromatographic analysis of the aldehyde phase separated off indicates the following composition:

| 3,5,5-trimethyl-1-hexanal | 91%; | 2-t-butyl-3-methyl-1-butanal | 2.5%; |
|---|---|---|---|
| 2,4,4-trimethyl-1-pentene | 1.5%; | 2,4,4-trimethyl-2-pentene | 3.2%; |
| 2,4,4-trimethylpentane | 0.2%; | 3,5,5-trimethyl-1-hexanol | 0.4%; |
| nonvolatile compounds | 1.2%. | | |

EXAMPLE 12

The procedure of Example 10 is repeated, but the 2,4,4-trimethyl-1-pentene is replaced by the same amount of an industrial mixture, known as diisobutylene, consisting of 76% of 2,4,4-trimethyl-1-pentene and 24% of 2,4,4-trimethyl-2-pentene.

The aldehyde phase separated off has the following composition:

| 3,5,5-trimethyl-1-hexanal | 93%; | 2-t-butyl-3-methyl-1-butanal | 1.5%; |
|---|---|---|---|
| 2,4,4-trimethyl-1-pentene | 1.5%; | 2,4,4-trimethyl-2-pentene | 2.2%; |
| 2,4,4-trimethylpentane | 0.2%; | 3,5,5-trimethyl-1-hexanol | 0.4%; |
| nonvolatile compounds | 1.2%. | | |

What is claimed is:

1. A process for preparing linear and branched aliphatic monoaldehydes having from 6 to 21 carbon atoms and cyclic aliphatic monoaldehydes having from 6 to 13 carbon atoms by reacting linear and branched aliphatic monoolefins having from 5 to 20 carbon atoms or cyclic olefins having from 5 to 12 carbon atoms with a carbon monoxide/hydrogen gas mixture using a rhodium catalyst, wherein the reaction is carried out in a heterogeneous phase by means of a rhodium (tripolyethylene glycolate) of a polyethylene glycol having a mean molecular weight of from 320 to 650 at a temperature of from 50 to 150° C. and a pressure of from 60 to 200 bar.

2. The process as claimed in claim 1, wherein the reaction is carried out in water, in a polyethylene glycol or a polyethylene glycol/water mixture as solvent, in each case using a polyethylene glycol having a mean molecular weight of from 320 to 650.

3. The process as claimed in claim 1, wherein a linear or branched monoolefin having from 6 to 18 carbon atoms is used in the reaction.

4. The process as claimed in claim 1, wherein a linear or branched monoolefin having from 10 to 20 carbon atoms is used in the reaction.

5. The process as claimed in claim 1, wherein the polyethylene glycol or glycolate has a mean molecular weight of from 350 to 450.

6. The process as claimed in claim 1, wherein the reaction is carried out at a temperature of from 80 to 120° C.

7. The process as claimed in claim 1, wherein the reaction is carried out at a pressure of from 75 to 120 bar.

8. The process as claimed in claim 1, wherein the reaction is carried out in the presence of up to 0.5% by weight, based on the olefin, of a secondary or tertiary amine or a cyclic amine.

9. The process as claimed in claim 8, wherein the amine is a dialkylamine having alkyl radicals of from 1 to 4 carbon atoms each or a trialkylamine having alkyl radicals of from 1 to 4 carbon atoms each.

10. The process as claimed in claim 8, wherein the amine is piperidine, pyridine or 3-methylpyridine.

11. A rhodium tri(polyethylene glycolate) of a polyethylene glycol having a mean molecular weight of from 320 to 650.

12. A rhodium tri(polyethylene glycolate) as claimed in claim 11 derived from a polyethylene glycol having a mean molecular weight of from 350 to 450.

13. A process for preparing a rhodium tri(polyethylene glycolate) as claimed in claim 11, which comprises heating rhodium(III) chloride trihydrate at a temperature of from 40 to 80° C. with a stoichiometric amount of a polyethylene glycol having a mean molecular weight of from 320 to 650.

14. A solution of a rhodium tri(polyethylene glycolate) as claimed in claim 11 in water, in polyethylene glycol having a mean molecular weight of from 320 to 650 or in a mixture thereof.

15. A method for the hydroformylation of alkenes and cycloalkenes to form alkanals and cycloalkanals, the improvement comprising using as the catalyst for the synthesis a rhodium tri (polyethylene glycolate) of a polyethylene glycol of claim 11.

* * * * *